United States Patent [19]

Linhardt et al.

[11] Patent Number: 4,916,219

[45] Date of Patent: Apr. 10, 1990

[54] OLIGOSACCHARIDE HEPARIN FRAGMENTS AS INHIBITORS OF COMPLEMENT CASCADE

[75] Inventors: Robert J. Linhardt; John M. Weiler, both of Iowa City, Iowa

[73] Assignee: University of Iowa Research Foundation, Iowa City, Iowa

[21] Appl. No.: 227,357

[22] Filed: Aug. 2, 1988

Related U.S. Application Data

[63] Continuation-in-part of Ser. No. 717,213, Mar. 28, 1985, abandoned.

[51] Int. Cl.$^4$ .................... A01N 43/04; C08B 37/10; C07G 37/00; C07H 1/00
[52] U.S. Cl. .................................. 536/21; 536/54; 536/118; 536/126; 536/122
[58] Field of Search .............. 514/56; 536/21, 54, 536/55.2, 55.3, 118, 119, 122, 126, 121

[56] References Cited

U.S. PATENT DOCUMENTS

| | | | |
|---|---|---|---|
| 3,636,202 | 1/1972 | Klein | 514/56 |
| 3,766,167 | 10/1973 | Lasker et al. | 536/54 |
| 3,873,614 | 3/1975 | Lamberti et al. | 536/105 |
| 4,021,544 | 5/1977 | Nair et al. | 536/4.1 |
| 4,098,995 | 7/1978 | Nair et al. | 536/54 |
| 4,240,163 | 12/1980 | Galin | 623/6 |
| 4,401,662 | 8/1988 | Lormeau et al. | 536/21 |
| 4,607,025 | 8/1986 | Petitou et al. | 514/56 |
| 4,788,307 | 11/1988 | Lormeau et al. | 536/21 |
| 4,847,338 | 7/1989 | Linhardt et al. | 536/54 |

FOREIGN PATENT DOCUMENTS

| | | |
|---|---|---|
| EP-A-163582 | 5/1985 | European Pat. Off. |
| 59-134774 | 6/1984 | Japan . |
| 0134502 | 7/1983 | United Kingdom .............. 514/56 |
| 0133078 | 2/1985 | United Kingdom .............. 536/21 |

OTHER PUBLICATIONS

Linker, *Biochem. J.* 183:711–720, 1979.
Sharath et al., *Immunopharmacology* 9:73–80, 1985.
Linhardt et al., *Appl. Biochem. Biotech.* 12:135–176, 1986.

*Primary Examiner*—Ronald W. Griffin
*Assistant Examiner*—Everett White
*Attorney, Agent, or Firm*—Seed and Berry

[57] ABSTRACT

There is disclosed oligosaccharide compounds having heparin-like anticomplement activity and reduced anticoagulant activity as compared with heparin on a weight or molar basis. The oligosaccharide compounds have at least 5 and no greater than 25 saccharide units. The oligosaccharides can have an even nuber of saccharide units with a terminus nonreducing sugar, or an odd number of saccharide units without a terminus nonreducing sugar. There is also disclosed anticomplement pharmaceutical compositions with reduced anticoagulant side effect activity and a process for preparing the oligosaccharide compounds.

22 Claims, 5 Drawing Sheets

OLIGOSACCHARIDE HEPARIN FRAGMENTS AS INHIBITORS OF COMPLEMENT CASCADE

TECHNICAL FIELD

This application is a continuation-in-part of U.S. patent application Ser. No. 717,213, filed Mar. 28, 1985, now abandoned.

The present invention relates to compounds and pharmaceutical compositions for inhibiting complement cascade without undue side effects of anticoagulant activity. The compounds are small chain fragments of the larger polysaccharides heparin of from about 6 saccharide units to about 24 saccharide units.

BACKGROUND OF THE INVENTION

Heparin is a highly sulfated, polydisperse, $\alpha$-(1→4)-linked copolymer of uronic acid and glucosamine. Jacques, *Science* 206: 528-33, 1979. Heparin is synthesized as a proteoglycan of approximately one million daltons molecular weight. Heparin is attached to a protein core. The protein core is removed in commercial processing, to obtain glucosaminoglycan heparin (average molecular weight 10,000 to 14,000 daltons).

Heparin's major application is as an anticoagulant. However, heparin has a multiplicity of other biological activities, including: (1) the ability to regulate angiogenesis (Folkman et al., *Science,* 221: 719-25, 1983); (2) the ability to regulate other cell growth and proliferation processes; (3) the ability to activate and release plasma lipoprotein lipase (Merchant et al., *Atherosclerosis,* 62: 151-58, 1986); and (4) the ability to inhibit complement cascade.

In 1929, Ecker and Gross first demonstrated the capacity of heparin to regulate complement activation. Subsequently, other investigators demonstrated multiple sites in the classical as well as the alternative-amplification pathways of complement at which heparin may act. Heparin's anticoagulant activity is mediated through a specific oligosaccharide sequence on the heparin polymer capable of binding antithrobin III. Heparin's structure activity relationship on the complement cascade system, however, is still poorly understood.

Heparin's complement cascade inhibiting activity can be used for a variety of functions to reduce the host's immune response. Organ transplant rejection is an example of an appropriate immune response which is detrimental to the individual host (i.e., mammals). Similarly, there are a variety of autoimmune diseases which result from the immune response attacking the individual's own cells. These immune and autoimmune diseases represent a class of diseases which are often difficult to treat effectively. Although there are a number of drugs which can be immune suppressant, none of the currently available therapeutic agents are adequate to control or specifically inhibit complement cascade activation. The inhibition of complement may be an important aspect in a variety of immune disorders. The diseases in which a substance that inhibits the complement cascade system may be therapeutically useful include paroxysmal nocturnal hemoglobulimurea, rheumatoid arthritis (in which the substance might be administered directly into a joint capsule to prevent complement activation), and hereditary angioedema (in which a deficiency in complement control protein leads to an active complement consumption). Other diseases include septic shock, rheumatoid arthritis and systemic lupus erythematous.

Heparin's anticoagulant activity has been demonstrated to be associated with the presence in its structure of a specific oligosaccharide sequence for the binding of antithrombin III. Once bound to heparin, antithrombin III can then inhibit a number of blood coagulation factors, and thus prevent the coagulation of blood.

Heparin's anticomplement activity is mediated by binding to a variety of complement cascade proteins and thereby regulates both the classical and alternate cascade pathways. Heparin and heparin oligosaccharides inhibit a portion of the complement cascade by inhibiting the generation of cell-bound amplification pathway C3 convertases, C3b,Bb, C3b,Bb,P and C3b,Bb,Nef. Heparin's anticomplement activity interferes with the binding site on the C3b. Furthermore, heparin prevents the fluid phase consumption of B by D in the presence of C3b, again indicating a direct action on C3b.

Accordingly, there is a need in the art for therapeutic agents with heparin-like anticomplement activity and greatly reduced (e.g., 10% or less) of heparin's anticoagulant activity on a weight basis. This invention fulfills the need.

TERMINOLOGY

The complement abbreviations used herein are C3 for the third complement protein, C3b for the activated third complement protein, C4b for the activated fourth complement protein, B, P and D are letter components of the alternative amplification pathway of complement. Other abbreviations include EAC4b,3b for the sheep erythrocyte cellular intermediate containing surface C4b and C3b. EAC4b,3b[5], EAC4b,3b[20], and EAC4b,3b[100] refer to cellular intermediates produced from EACl,4b using 5 $\mu$g, 20 $\mu$g, and 100$\mu$ per $1 \times 10^9$ EACl,4b. For the saccharides, $\Delta$UA refers to 4-deoxy-$\alpha$-L-threo-hex-4-enopyronosyluronic acid (a nonreducing sugar); p refers to pyranose; GlcA refers to glucuronic acid; IdoA refers to iduronic acid; and S refers to sulfate.

DISCLOSURE OF THE INVENTION

Briefly stated, the present invention comprises heparin oligosaccharide fractions having degrees of polymerization from about 6 to about 24 saccharide units. The oligosaccharides of the present invention can have an even number of saccharide units, wherein groups of saccharide units are disaccharides, tetrasaccharides and hexasaccharides.

The present invention also comprises heparin oligosaccharide fractions having an odd-number degree of polymerization from about 5 to about 23 saccharide units wherein the nonreducing terminus ($\Delta$UAp) saccharide is removed. Removal of the nonreducing terminus saccharide can be accomplished by treatment of the even-numbered oligosaccharide, as described herein, with ozone at an acidic pH.

Preferably, the disaccharide group of saccharide unit is a trisulfated disaccharide such as $\Delta$UAp2S(1→4)-$\alpha$-D-GlcNp2S6S (2 in Table 1 and where n=0 in Formula I). The tetrasaccharide group of saccharide unit is selected from the group consisting of pentasulfated tetrasaccharides, such as $\Delta$UAp2S(1→4)-$\alpha$-D-GlcNp2S(1→4)-$\alpha$-L-IdoAp2S-$\alpha$-D-GlcNp2S6S (4A in Table 1) and $\Delta$UAp2S(1→4)-$\alpha$-D-GlcNp2S6S(1→4)-$\beta$-D-GlcAp(1→4)-$\alpha$-D-GlcNp2S6S (4B in Table 1), and hexasulfated tetrasaccharides, such as ΔUAp2S(1→4)-α-D-GlcNp2S6S(1→4)-α-L-IdoAp2S(1→4)-α-D-GlcNp2S6S (4C in Table 1); and the hexasaccharide group of saccharide unit is a septasulfated hexasaccharide, such as ΔUAp2S(1→4)-α-D-GlcNp2S6S(1→4)-α-L-IdoAp(1→4)-α-D-GlcNAcp6S-(1→4)-β-D-GlcAp(1→4)-α-D-GlcNp2S3S6S (6C in Table 1).

An example of a trisulfated disaccharide is 4-deoxy-α-L-threo-hex-4-enopyronosyluronic acid-2-sulfate linked 1→4 to α-D-2-deoxy-2-amino-glucopyronosyl-2,6 disulfate, wherein α and β represent the anomeric configurations of the sugars and D and L represent the absolute configuration of the sugars.

Most preferably, the hexasaccharide, octasaccharide and decasaccharide are tri-, tetra- and pentaoligomers of the heparin disaccharide (2), which is a trisulfated disaccharide, such as decasaccharide 10D (in Table 1) which has the structure $(2)_5$.

The process of the present invention prepared groups of saccharide units polymerized to form an oligosaccharide with an even-numbered degree of polymerization of from about 6 to about 24 saccharide units. The invention process further comprises the step of removing the terminus nonreducing sugar to form an odd-numbered degree of polymerization saccharide with from about 5 to about 23 saccharide units.

The oligosaccharides of the present invention have strong anticomplement activity, to being equipotent with heparin on a molar basis. The oligosaccharides of the present invention also have reduced anticoagulant activity, defined as less than 10% of heparin's anticoagulant activity on a weight basis.

DETAILED DESCRIPTION OF THE INVENTION

The partial enzymatic depolymerization of heparin produced a controlled and reproducible distribution of heparin-oligosaccharides of the formula:

Formula I wherein R is a metallic or non-metallic cation or hydrogen or a free acid, X is H or $SO_3R$, Y is H, $COC_{1-6}$ alkyl or $SO_3R$, and n is an integer from about 1 to about 11. Preferably, Y is $COCH_3$, n is 4 and R is hydrogen, sodium or potassium.

Heparin oligosaccharides having a degree of polymerization of 6 units to 24 units and formed by polymerizing 2, 4 or 6 saccharide unit complexes were found to have complement inhibiting activity potency comparable to native heparin on a weight basis and very little or no anticoagulant activity.

Figure 1:
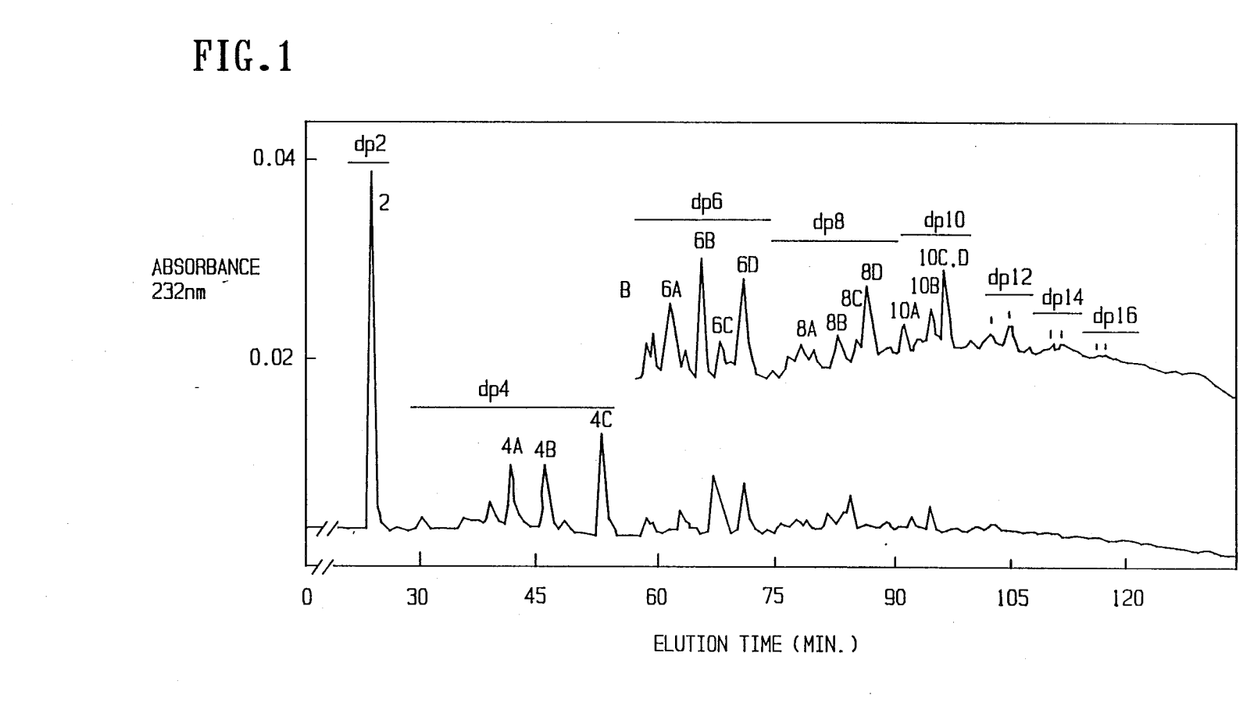
FIG. 1 shows the strong anion-exchange-HPLC of a heparin-oligosaccharide mixture prepared by heparinase-catalyzed depolymerization of heparin to 30% reaction completion. Absorbance at 232 nm of 1 mg (A) and 4 mg (B) of heparin-oligosaccharide sample eluting from the column are plotted against elution time in minutes. The peaks collected from the column are labeled to identify the sample (sample number corresponds to degree of polymerization).

At 30% reaction completion, the heparin-oligosaccharide mixture contained the maximum number in concentration of heparin-oligosaccharides with degrees of polymerization between 10 and 24 saccharide units, wherein all the heparin-oligosaccharides contained an even number of saccharide units. The oligosaccharide mixture is fractionated on the basis of charge using strong anion exchange-HPLC (as shown in FIG. 1) to obtain purified heparin-oligosaccharide samples of a defined degree of polymerization and containing a single major component. The elution order from the HPLC column was dependent on the degree of polymerization (i.e., disaccharide followed by tetrasaccharide, followed by hexasaccharide, etc.), and within each size group, elution order was dependent on degree of sulfation (i.e., tetrasaccharide 4A and 4B in Table 1 having 5 sulfates, followed by tetrasaccharide 4C having 6 sulfates). The refractionation of the oligosaccharide components produced heparin-oligosaccharides of sufficient purity to obtain a compositional analysis as shown in Table 1 below.

TABLE 1

Structure of Heparin Oligosaccharides Having Degree of Polymerization from 6 to 10

| Heparin Oligosaccharide | Oligosaccharide[a,b] Composition | Mol. Wt. | Number of Sulfate Groups |
|---|---|---|---|
| 6A | 2,4A | 1893 | 8 |
| 6B | 2,4B | 1893 | 8 |
| 6D[c] | 2,4C | 1995 | 9 |
| 8A | 2,2,4A | 2456 | 11 |
| 8B | 2,2,4B | 2456 | 11 |
| 8C | 2,6C | 2498 | 10 |
| 8D[c] | 2,2,4C | 2660 | 12 |
| 10A | 2,2,2,4A | 3223 | 14 |
| 10B | 2,2,2,4B | 3223 | 14 |
| 10C | 2,2,6C | 3163 | 13 |
| 10D[c] | 2,2,2,4C | 3325 | 15 |

[a]No sequence is implied by the order of the fundamental oligosaccharide components.
[b]The structures of the fundamental oligosacchrides making up each transient oligosaccharide are:
2,trisulfated disaccharide,ΔUAp2S(1 → 4)-α-D-GlcNp2S6S;
4A,pentasulfated tetrasaccharide,ΔUAp2S(1 → 4)-α-D-GlcNp2S(1 → 4)-α-D-GlcNp2S6S;
4B,pentasulfated tetrasaccharide,ΔUAp2S(1 → 4)-α-D-GlcNp2S6S(1 → 4)-β-D-GlcAp(1 → 4)-α-D-GlcNp2S6S;
4C,hexasulfated tetrasaccharide,ΔUAp2S(1 → 4)-α-D-GlcNp2S6S(1 → 4)-α-L-IdoAp2S(1 → 4)-α-D-GlcNp2S6S;
6C,septasulfated hexasaccharide,ΔUAp2S(1 → 4)-α-D-GlcNp2S6S(1 → 4)-α-L-IdoAp(1 → 4)-α-D-GlcNAcp6S-(1 → 4)-β-D-GlcAp(1 → 4)-α-D-GlcNp2S3S6S.
[c]The oligosaccharide composition of this heparin-oligosaccharide can only be arranged in one way since 4C = 2,2 thus this oligosaccharide's sequence is established.

Only one sequence is possible for hexasaccharide 6D, octasaccharide 8D, and decasaccharide 10D, since their compositional analysis indicated that they were simply oligomers of heparin disaccharide 2.

The compounds of the present invention are characterized by the capacity to inhibit complement activation, while having little or no anticoagulant activity, as shown in Table 2.

Oligosaccharides with degrees of polymerization from about 2 to about 24 saccharide units can be prepared by partial depolymerization of heparin using heparinase. The degree of depolymerization (i.e., percent reaction completion) can be varied from about 1% to about 100% to optimize the production of an oligosaccharide having a particular size or degree of polymerization. Following partial or complete depolymerization, the oligosaccharide mixture is fractionated using a strong anion exchange HPLC column or other suitable techniques, such as polyacrylamide gel electrophoresis (See, Rice et al., Biochem J., 244: 515–22 (1987)). Refractionation by one or a combination of these techniques results in a highly purified oligosaccharide. Oligosaccharides of greater than six saccharide units (i.e., molecular weight greater than 1000 daltons) is desalted by exhaustive dialysis against deionized water using controlled pore dialysis membranes.

TABLE 2

Anticoagulant activity of heparin-oligosaccharides.

| Heparin Oligosaccharide | ACTIVITY[a] (units/μmole) | | |
|---|---|---|---|
| | aPTT | Antithrombin III mediated Anti-factor IIa | Anti-factor Xa |
| 2 | <1 | <1 | <0.1 |
| 4A | 2 | <1 | <0.1 |
| 4B | 2 | <2 | 0.1 |
| 4C | 2 | <2 | 3 |
| 6A | nd[b] | <2 | <2 |
| 6B | nd | <2 | 4 |
| 6C | 26 | 11 | 26 |
| 6D | 11 | <2 | 4 |
| 8A | 16 | <3 | 118 |
| 8B | 21 | <3 | 25 |
| 8C | nd | <3 | 29 |
| 8D | 22 | <3 | 32 |
| 10A | 37 | <3 | nd |
| 10B | 45 | <3 | 116 |
| 10C | nd | <3 | 61 |
| 10D | 54 | <3 | 136 |
| Heparin | 2,338 | 2,338 | 2,338 |

[a]Activity is determined based on a standard curve using heparin (Mr avg 14,000) with an activity of 167 units/mg.
[b]nd, not determined The compounds of the present invention are obtained by depolymerizing heparin with the lyase enzyme, heparinase. The mixture of oligosaccharides obtained by the heparinase digestion have the desired anticomplement activity and have significantly reduced or no anticoagulant activity as compared with native heparin on a weight or molar basis. The oligosaccharides that are produced by heparinase digestion and subsequent purification have from about 6 to about 24 saccharide units and contain an even number of saccharide units. Preferably, the oligosaccharids have 16 to 24 saccharide units. Most preferably, the oligosaccharide is a 24 saccharide oligosaccharide.

The compounds of the present invention also include a complimentary series of oligosaccharides having an odd number of saccharide units, from about 5 to 23 saccharide units, and prepared by treating the even-numbered oligosaccharide of the present invention with ozone under acidic conditions to remove the terminus nonreducing sugar.

The following examples illustrate the synthesis of the oligosaccharides and their anticomplement and anticoagulant activity. The examples are offered by way of illustration and not limitation.

EXAMPLE 1

Heparin-oligosaccharides were prepared with heparinase (0.25 unit of purified enzyme as 50 units/mg) or as commercial enzyme (0.23 units/mg). Heparinase was added to 300 mg of heparin (from a commercial source, such as porcine mucosal or bovine lung heparin) in 37.5 ml of 250 mM sodium acetate, 2.5 mM calcium acetate solution at pH 7.0. The mixture was incubated at 30° C. for 40 hours. Aliquots were removed periodically and the absorbance was measured at 232 nm after diluting the sample 100-fold in 0.03N hydrochloric acid. The reaction was terminated after approximately 30% completion by heating the reaction mixture to 100° C. for one minute. The product was frozen at −70° C., freeze-dried and reconstituted with distilled water to a volume of 4 mL. The reconstituted sample was then desalted on Sephadex G-10, collected, freeze-dried and reconstituted with 6 mL of distilled water to a final concentration of 50 mg/mL.

The partial enzymatic depolymerization of heparin produced a controlled and reproducible distribution of heparin-oligosaccharides at 30% reaction completion, the mixture contained the maximum number and concentration of heparin-oligosaccharides with degrees of polymerization between about 10 and about 16 saccharide units. This mixture also contained heparin-oligosaccharides with degrees of polymerization of 2 to 10 saccharide units and degrees of polymerization of 16 to 24 saccharide units in sufficient quantities to lead to their purification. If heparin-oligosaccharides of degrees of polymerization of 2 to 10 saccharide units are required, it is desirable to terminate the reaction at between 50 and 75% completion. If heparin-oligosaccharides of degrees of polymerization of 16 to 24 saccharide units are required, it is desirable to terminate the reaction at 10 to 20% completion.

EXAMPLE 2

This example illustrates the fractionation of heparin-oligosaccharides. The heparin-oligosaccharide mixture (20 mg) was injected into a strong anion exchange HPLC semi-preparative column, pre-equiliberated with 0.2M sodium chloride at pH 3.5 at a flow rate of 1.5 mL/min. A linear salt gradient was begun immediately using sodium chloride at pH 3.5 at 1.5 mL/min. flow rate. Fractions from each peak were combined, freeze-dried, reconstituted with 4 mL of distilled water and desalted either by Sephadex G-10 gel permeation chromatography on a 3 cm×45 cm column at a flow rate of 3 mL/min. (samples with degree of polymerization of less than 6), or by dialysis against 3×1000 volumes of deionized water (samples with degree of polymerization greater than 6). The samples were freeze-dried and stored at −70° C.

The results of the fractionation on the basis of charge was the obtaining of purified heparin-oligosaccharide samples of a defined degree of polymerization and containing a single major component. Elution order from the anion exchange-HPLC column, as shown in FIG. 1, was dependent on the degree of polymerization (i.e., disaccharide (2) followed by tetrasaccharides, followed by hexasaccharides, etc.). Within each size group, elution order was dependent on degree of sulfation (i.e., tetrasaccharide 4A and 4B having five sulfates followed by tetrasaccharide 4C having six sulfates). This method of fractionation is suitable to prepare purified heparin-oligosaccharides with degrees of polymerization between 2 and 24 saccharide units.

EXAMPLE 3

This example illustrates the quantitation and analysis of the heparin-oligosaccharides. Freeze-dried samples were dissolved in distilled water to a volume of 1 mL and aliquots of each were removed, added to 0.03N hydrochloric acid and the absorbance was measured at 232 nm. The concentration of each sample was then estimated based upon its molecular weight. Molecular weight was calculated either directly from its chemical structure or estimated from its degree of polymerization as measured by gel permeation HPLC (See, Sharath et al., *Immunopharmacology* 9: 73–83 (1985)) and a molar absorptivity value of $5.2 \times 10^3 M^{-1}$ cm.

The more concentrated samples were further diluted until all the samples were at approximately the same concentration (1 mg/mL). Quantitation of the 1 mg/mL stock solutions relied on uronic acid determination by carbazole assay against a standard curve constructed using the heparin from which they were prepared. The compositional analysis is shown in Table 1 herein.

EXAMPLE 4

This example illustrates the activity of heparin and heparin-oligosaccharides to inhibit generation of the alternative-amplification pathway C3 convertase. The method described in Weiler et al., *J. Exp. Med.* 147: 409–421, 1978; Weiler, *Immunopharmacology* 6: 245–255, 1983; and Sharath et al., *Immunopharmacology* 9: 73–83, 1985, was used. Briefly, inhibition was examined in experiments that used EAC4b,3b which were prepared to have high, intermediate, and low amounts of C3 on the cell surface. $EAC4b,3b^{100}$, $EAC4b,3b^{20}$, and $EAC4b,3b^5$ were produced using a C3 input of 100 μg, 20 μg, and 5 μg per $10^9$ EAC4b,2a cellular intermediates, respectively. Complement assay buffer (DGVB++) 100 μL, alone was added to tubes used for the reagent blank, no inhibition, and 100% lysis; or complement assay buffer containing a heparin or heparin-oligosaccharide solution was added to the remaining tubes. At time zero, 100 μl of complement assay buffer containing a suspension of $1 \times 10^7$ EAC4b,3b, an excess amount of P and D (100 ng P), and an amount of B needed to lyse the noninhibited tubes at an average of 1 hemolytic event per cell (0.03 ng B for $EAC4b,3b^{100}$, 0.15 ng B for $EAC4b,3b^{20}$, and 0.50 ng B for $EAC4b,3b^5$) was added to each tube. The tubes used for the reagent blank contained no B. The mixtures were incubated for 30 minutes at 30° C. with shaking. Then, 300 μL of a 1:20 dilution of rat serum in 40 mM EDTA was added to each tube and incubation was continued with shaking for 60 minutes at 37° C. Saline (1.5 mL) was then added to each tube, except the 100% tube which was lysed with 1.5 mL of water in place of the saline. Finally, the contents of the tubes were mixed, centrifuged and the absorbance of the supernatant was measured at 414 nm.

The percent lysis, the average number of hemolytic sites per cell (Z), and the percent inhibition were then calculated. Data are expressed as either percent inhibition or as 100 times the ED50 (the amount of heparin resulting in 50% inhibition) for heparin divided by the ED50 for heparin-oligosaccharide. Concentration of heparin and heparin-oligosaccharides are expressed as micrograms per $1 \times 10^7$ cellular intermediates. The volume of the reaction tubes during convertase generation varied between 0.2 mL and 0.3 mL; the number of cellular intermediates was held at $1 \times 10^7$ per tube. The amount of lysis (Z) seen in the nonhibited tube was relatively independent of the volume of buffer present in the tube during convertase generation. Similarly, the amount of inhibition of convertase generation was independent of the volume of buffer present in the tube during convertase generation.

The results of this experiment demonstrate that heparin's inhibitory activity was reduced as C3b loading was increased. In this experiment, the amount of B input was increased as the concentration of C3b on the cellular intermediate was decreased in order to maintain an average of 1 hemolytic event per cell (Z). The experiments determined whether the B input alone might play a role in determining the degree of inhibition of heparin to interfere with the assembly of effective convertase on $EAC4b,3b^{20}$ in the presence of low, moderate and high concentrations of B. The amount of B present in the cellular intermediates did not have any affect on the ability of heparin or heparin-oligosaccharide to inhibit lysis.

Figure 2:
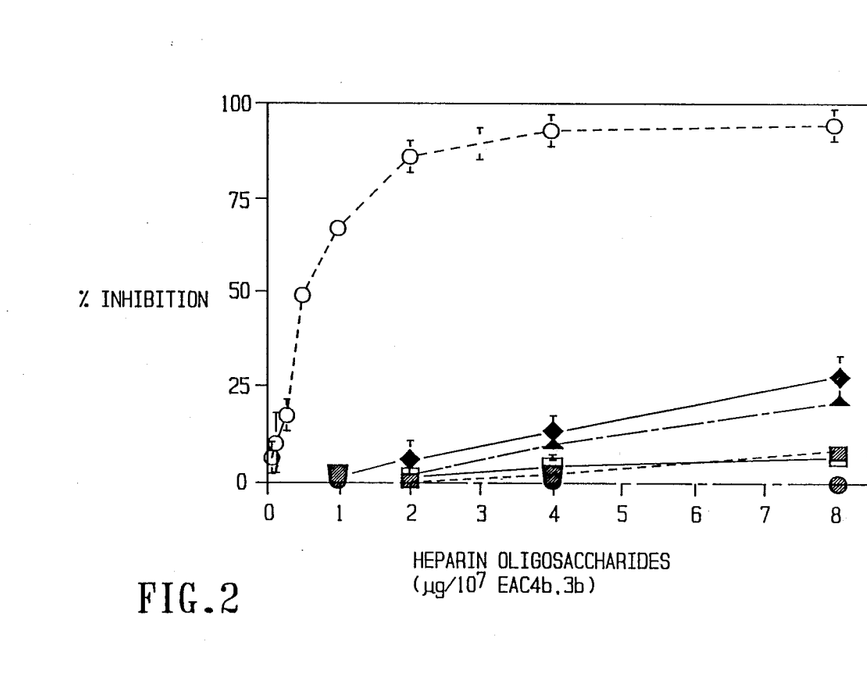
FIG. 2 shows the effect of heparin and structurally characterized heparin-oligosaccharides on the alternate-amplification pathway of complement. A dose response curve is shown for heparin (○); septasulfated hexasaccharide-6A (◆), hexasulfated tetrasaccharide-4C (▲), pentasulfated tetrasaccharide-4B (□), and trisulfated disaccharide-2 (●).
Figure 3:
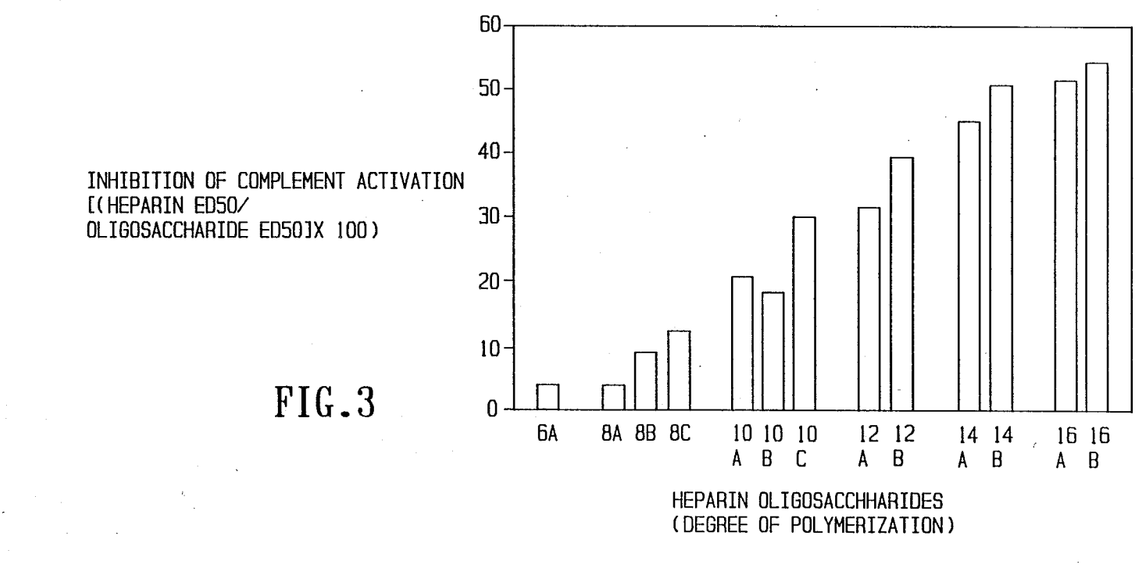
FIG. 3 shows the inhibition of lysis of EAC4b,3b[100] by heparin-oligosaccharides. Activity is expressed as [(ED50 heparin/ED50 heparin-oligosaccharide)×100]. ED50 is measured on a molar basis using an average molecular weight for heparin of 14,000.

The results of the experiment in FIG. 2 illustrate the regulation of complement activation by heparin-oligosaccharides using a disaccharide, tetrasaccharides 4A, 4B, and 4C, and a hexasaccharide 6C of the sequences defined in Table 1 herein. The oligosaccharide samples exhibited low activity for complement activation giving linear dose response curves from 1 to 8 μg per $10^7$ cellular intermediates (FIG. 2). Heparin-oligosaccharides of higher degrees of polymerization, from 6 to 16 saccharide units, having molecular weights ranging from 1893 to 5320, were then tested for activity. The results were compared with native heparin's activity on a weight basis. A high molecular weight heparin-oligosaccharide (16B, molecular weight 5320) was 54% as potent as native heparin on a molar basis and 130% on a weight basis.

Heparin oligosaccharides having as many as 24 saccharide units were prepared according to the methods described herein. The oligosaccharides had greatly reduced anticoagulant activity (defined as less than 10% of native heparin's anticoagulant activity on a weight basis). The heparin oligosaccharides were tested for the ability to regulate complement activation as described herein. An oligosaccharide with 24 saccharide units was equipotent with heparin on a molar basis.

Figure 4:
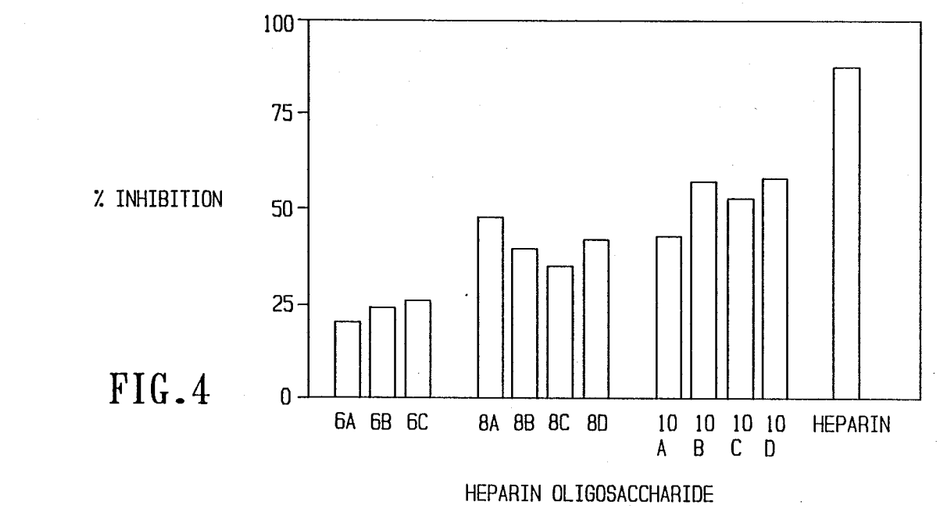
FIG. 4 depicts the inhibition of the generation of amplification pathway C3 convertase on EAC4b,3b[20] by 4 μg of heparin and homogeneous structurally defined heparin-oligosaccharides. The heparin oligosaccharides 6A, 6B, 6C, 8A, 8B, 8C, 8D, 10A, 10B, 10C, and 10D are defined in Table 1 herein.

This example also illustrates the relationship of oligosaccharide structure to complement regulatory activity. Eleven pure heparin-oligosaccharides of defined compositions ranging in size from hexasaccharide through decasaccharide (FIG. 4) were examined. These homogeneous heparin-oligosaccharides displayed less anticoagulant activity and virtually identical complement activation inhibitory activity as compared to their less purified counterparts.

EXAMPLE 5

Figure 5:
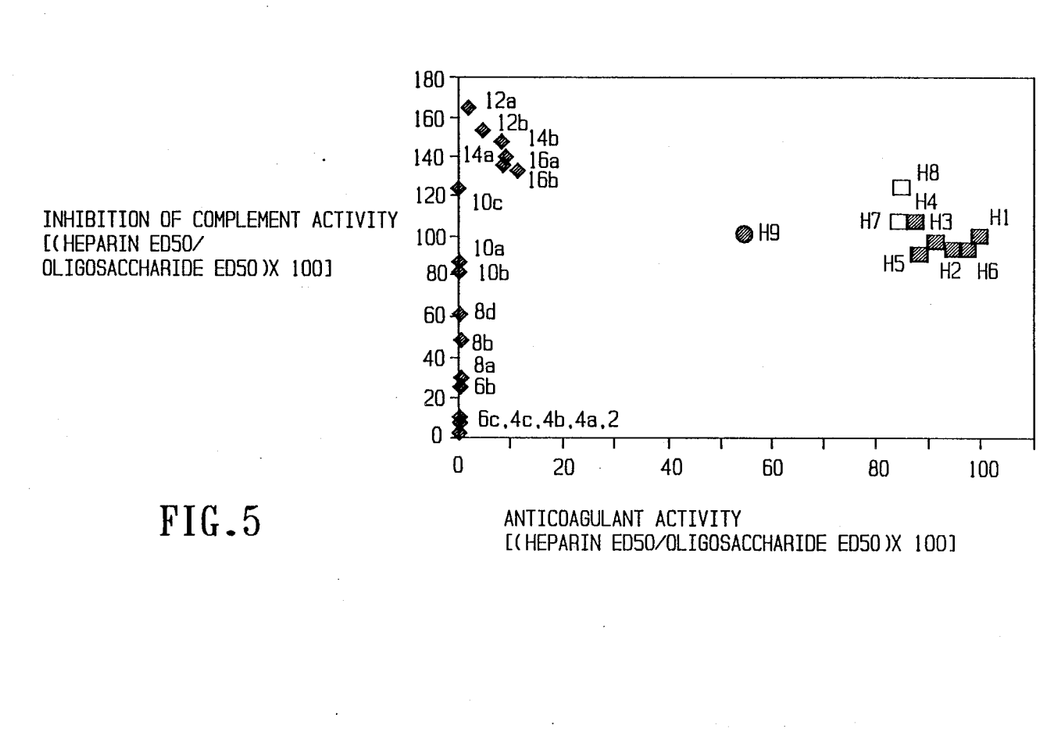
FIG. 5 shows the inhibition of lysis of EAC4b,3b[100] by various commercial heparins and heparin-oligosaccharides (shown in Table 1) plotted against anticoagulant activity. Anticoagulant activity was measured by anti-factor IIa amidolytic assay relative to a standard porcine heparin (H1) on a weight basis, as shown in Table 2. Inhibition of complement activity is expressed as [(ED50 heparin/ED50 heparin-oligosaccharide)×100] on a weight basis. Porcine heparins (■H1→H6), bovine heparins (□H7,H8), low molecular weight heparin (●H9) and heparin-oligosaccharides (◆2→16b) are identified by the adjacent number.

This example illustrates the anticoagulant activity of each heparin and heparin-oligosaccharide fragment. Anticoagulant activity was determined by aPTT (activated thromboplastin time) (Linhardt et al., *J. Biol. Chem.* 257: 7310-13, 1982). Antithrombin III-mediated anti-factor IIa and antifactor Xa activity was measured using purified plasma proteins as described in Linhardt et al. and in Table 2. As shown in FIG. 5, five porcine heparins showed activities ranging from 90% to 107% of standard porcine heparin (H1) on a weight basis. Two bovine heparins had 106% and 124% of standard porcine heparin's activity and the low molecular weight heparin had 100% of standard porcine heparin's activity on complement activation.

The anticoagulant activity of the heparin-oligosaccharides and commercial heparins using activated partial thromboplastin time and antithrombin III-mediated anti-factor IIa assays gave similar results, with the antifactor IIa assay demonstrating slightly lower values (Table 2). The anticoagulant activity of heparin-oligosaccharides and commercial heparins measured by antifactor IIa assays are plotted against their ability to inhibit complement activation in FIG. 5. The porcine heparins, bovine heparins, and low molecular heparins cluster, showing only minor differences in activities. By contrast, the heparin-oligosaccharides showed a slight increase in anticoagulant activity with a marked increase in complement-regulating activity as the degree of polymerization increased.

EXAMPLE 6

This example illustrates a process for the removal of the ΔUAp saccharide unit from the nonreducing end of heparinase (EC 4.2.2.7)-prepared heparin oligosaccharides having an even number of saccharide units. This process produces a complementary set of heparin oligosaccharides with an odd number of saccharide units. A heparin oligosaccharide of from 6 to 24 saccharide units is dissolved at 100 μg/mL in 0.03N hydrochloric acid. Ozone gas is bubbled through this solution until the solution absorbance at 232 nm is eliminated. The solution pH is adjusted to pH 7.0 and the low molecular weight fragments of the ΔUAp saccharide unit are removed by gel permeation chromatography on a Sephadex 6-15 column. The heparin oligosaccharide having an odd number of saccharide units is recovered and quantitated using an uronic acid.

Although the foregoing invention has been described, in part, by way of illustration and example for the purposes of clarity and understanding, it will be appreciated that certain changes or modifications will be practiced without deviating from the spirit and scope of the invention.

We claim:

1. An oligosaccharide of the formula:

wherein R is a metallic or nonmetallic cation, X is $SO_3R$, and n is an integer from 5 to 11, wherein said oligosaccharide has heparin-like anticomplement activity, wherein said oligosaccharide has reduced anticoagulant activity as compared with heparin, and wherein the sodium salt of the oligosaccharide contains at least 14% sulfur.

2. The oligosaccharide of claim 1 wherein R is selected from the group consisting of Na, K and Li.

3. The oligosaccharide of claim 1 wherein R is Na.

4. The oligosaccharide of claim 1 wherein n is from 5 to 7.

5. A pharmaceutical composition comprising an oligosaccharide of the formula:

wherein R is a metallic or nonmetallic cation, X is $SO_3R$, and n is an integer from 5 to 11, wherein the sodium salt of the oligosaccharide contains at least 14% sulfur; and an acceptable pharmaceutical carrier for parenteral administration.

6. The pharmaceutical composition of claim 5 wherein R is selected from the group consisting of Na, K and Li.

7. An oligosaccharide of the formula:

11. An odd-numbered oligosaccharide of the formula:

wherein R is a metallic or nonmetallic cation, X is $SO_3R$, and n is an integer from 5 to 7,
wherein said oligosaccharide has heparin-like anti-complement activity,
wherein said oligosaccharide has reduced anticoagulant activity as compared with heparin, and
wherein the sodium salt of the oligosaccharide contains at least 14% sulfur.

8. The oligosaccharide of claim 7 wherein R is selected from the group consisting of Na, K and Li.

9. A process for preparing an oligosaccharide with heparin-like anticomplement activity and reduced anticoagulant activity as compared with heparin, comprising:
  partially depolymerizing a heparin with the enzyme heparinase to obtain a polysaccharide mixture;
  fractionating the polysaccharide mixture by an anion exchange column and collecting the separated fractions;
  treating the separated fractions to form the disaccharide, tetrasaccharides and hexasaccharide identified in Table 1 as 2, 4A, 4B, 4C, and 6C; and
  polymerizing the disaccharide, tetrasaccharides and/or hexasaccharide to form an oligosaccharide with an even-numbered degree of polymerization of from 10 to 24 saccharide units.

10. The process of claim 9, further comprising a final step of removing the terminus nonreducing sugar of the even-numbered oligosaccharide by exposing the oligosaccharide to ozone in an acidic environment.

wherein R is H or a metallic or nonmetallic cation, X is H or $SO_2R$, y is H, $COC_{1-6}$ alkyl or $SO_3R$, and n is an integer from about 1 to about 11,
wherein said oligosaccharide has heparin-like anti-complement activity, and
wherein said oligosaccharide has reduced anticoagulant activity as compared with heparin.

12. The odd-numbered oligosaccharide of claim 11 wherein R is selected from the group consisting of H, Na, K and Li.

13. The odd-numbered oligosaccharide of claim 11 wherein n is 10 and the oligosaccharide has 23 saccharide units.

14. The odd-numbered oligosaccharide of claim 13 wherein R is H or Na.

15. The odd-numbered oligosaccharide of claim 14 wherein Y is $COCH_3$.

16. The odd-numbered oligosaccharide of claim 11 wherein n is an integer from about 4 to about 10.

17. A pharmaceutical composition comprising an odd-numbered oligosaccharide of the formula:

wherein R is H or a metallic or nonmetallic cation, X is H or $SO_2R$, y is H, $COC_{1-6}$ alkyl or $SO_3R$, and n is an integer from about 1 to about 11,
wherein said oligosaccharide has heparin-like anti-complement activity, and
wherein said oligosaccharide has reduced anticoagulant activity as compared with heparin.

18. The pharmaceutical composition of claim 17 wherein R is selected from the group consisting of H, Na, K and Li.

19. The odd-numbered oligosaccharide of claim 17 wherein n is 10 and the oligosaccharide has 23 saccharide units.

20. The odd-numbered oligosaccharide of claim 19 wherein R is H or Na.

21. The odd-numbered oligosaccharide of claim 20 wherein Y is $COCH_3$.

22. The odd-numbered oligosaccharide of claim 17 wherein n is from 4 to 10.

* * * * *